(12) United States Patent
Edwards et al.

(10) Patent No.: US 9,851,312 B2
(45) Date of Patent: Dec. 26, 2017

(54) BACKSCATTER INSPECTION SYSTEMS, AND RELATED METHODS

(71) Applicant: The Boeing Company, Chicago, IL (US)

(72) Inventors: William Talion Edwards, Wentzville, MO (US); Gary Georgeson, Tacoma, WA (US); James E. Engel, Newport Beach, CA (US); Morteza Safai, Newcastle, WA (US)

(73) Assignee: THE BOEING COMPANY, Chicago, IL (US)

( * ) Notice: Subject to any disclaimer, the term of this patent is extended or adjusted under 35 U.S.C. 154(b) by 325 days.

(21) Appl. No.: 14/272,177

(22) Filed: May 7, 2014

(65) Prior Publication Data

US 2015/0323477 A1  Nov. 12, 2015

(51) Int. Cl.
 *G01N 23/00*  (2006.01)
 *G01N 23/203*  (2006.01)
 *G21K 1/10*  (2006.01)

(52) U.S. Cl.
 CPC ............ *G01N 23/203* (2013.01); *G21K 1/10* (2013.01); *G01N 2223/313* (2013.01)

(58) Field of Classification Search
 CPC ................................ G21K 1/10; G01N 23/203
 See application file for complete search history.

(56) References Cited

U.S. PATENT DOCUMENTS 5,838,239 A * 11/1998 Stern ...................... B64D 15/20
340/583

6,377,652 B1 * 4/2002 Sturm ..................... G01N 23/06
378/157

(Continued)

OTHER PUBLICATIONS

Addicott, Benjamin Teichman, Characterization and Optimization of Radiography by Selective Detection Backscatter X-Ray Imaging Modality, A Thesis Presented to the Graduate School of the University of Florida in Partial Fulfillment of the Requirements for the Degree of Master of Engineering, pp. i-80, University of Florida, 2006, Gainesville, United States.

(Continued)

*Primary Examiner* — Dani Fox
(74) *Attorney, Agent, or Firm* — Patterson + Sheridan, LLP

(57) ABSTRACT

Inspection systems employing radiation filters with different attenuation characteristics to determine specimen irregularities, and related methods are disclosed. An inspection system includes a radiation emitter configured to emit a radiation beam along a radiation trajectory. Some of the radiation may be reflected by the specimen as backscatter and received by at least one radiation detector of the inspection system along the radiation trajectory. Irregularities and various materials of the specimen may produce backscatter radiation at different energies and/or scatter angles which may be identified by employing radiation filters having different attenuation characteristics. By employing these filters in communication with the radiation emitter and the radiation detector, the backscatter radiation passed through the filters may be measured and integrated at different positions of the radiation beam to produce a composite image of the specimen. In this manner, irregularities and associated materials within the specimen may be more easily identified.

18 Claims, 7 Drawing Sheets

(56) References Cited

U.S. PATENT DOCUMENTS

| | | | |
|---|---|---|---|
| 6,477,226 B1* | 11/2002 | Lehmann | B81B 1/00 378/143 |
| 7,463,714 B2 | 12/2008 | Edwards et al. | |
| 7,508,910 B2 | 3/2009 | Safai et al. | |
| 7,529,343 B2 | 5/2009 | Safai et al. | |
| 7,599,471 B2 | 10/2009 | Safai et al. | |
| 7,623,626 B2 | 11/2009 | Safai et al. | |
| 7,649,976 B2 | 1/2010 | Georgeson et al. | |
| 8,033,724 B2 | 10/2011 | Edwards et al. | |
| 8,094,781 B1 | 1/2012 | Safai et al. | |
| 2002/0186817 A1* | 12/2002 | Schukalski | G21K 1/04 378/156 |
| 2008/0037707 A1* | 2/2008 | Rothschild | G01N 23/046 378/57 |
| 2011/0220793 A1* | 9/2011 | Thomas | H01J 37/20 250/307 |
| 2012/0201356 A1* | 8/2012 | Rothschild | G01V 5/0025 378/87 |
| 2013/0279653 A1* | 10/2013 | Hansford | G01N 23/20091 378/46 |

OTHER PUBLICATIONS

Addicott, Benjamin Teichman, Characterization and Optimization of Radiography by Selective Detection Backscatter X-Ray Imaging Modality, A Thesis Presented to the Graduate School of the University of Florida in Partial Fulfillment of the Requirements for the Degree of Master of Engineering, University of Florida, 2006, pp. 81-181, Gainesville, United States.

Addicott, Benjamin Teichman, Characterization and Optimization of Radiography by Selective Detection Backscatter X-Ray Imaging Modality, A Thesis Presented to the Graduate School of the University of Florida in Partial Fulfillment of the Requirements for the Degree of Master of Engineering, University of Florida, 2006, Gainesville, United States.

* cited by examiner

BACKSCATTER INSPECTION SYSTEMS, AND RELATED METHODS

GOVERNMENT LICENSE RIGHTS

This invention was made with government support under Contract Number N00019-11-G-0001 awarded by The United States Department of Defense. The government has certain rights in the invention.

BACKGROUND

Field of the Disclosure

The present disclosure relates to non-destructive inspection systems and techniques, and more specifically, to radiation backscatter inspection.

Technical Background

Non-destructive inspection systems may be used during and after a product or sub-assembly has been created to ensure reliable and safe operation to specification. In this regard, these systems may detect irregularities which may prematurely reduce the useful lifespan of products. Examples of irregularities include wear, corrosion, foreign objects, and stress cracks. Some irregularities are more serious than others. Non-destructive inspection systems, for example conventional backscatter detectors, have been used to identify irregularities in various locations of products. However, depending upon the location and type of irregularity, there may be difficult cases when it may be impractical or inefficient for conventional backscatter inspection systems to be utilized because of an inability to easily distinguish irregularities associated with various materials of the product or sub-assembly. In these cases, alternative and more expensive inspections may be performed such as disassembly and statistical sampling using destructive testing. What is needed is a more effective approach to inspect products and subsystems to identify and distinguish irregularities associated with various materials.

SUMMARY

Embodiments enclosed herein include inspection systems employing radiation filters with different attenuation characteristics to determine specimen irregularities, and related methods. An inspection system includes a radiation emitter configured to emit a radiation beam along a radiation trajectory. Some of the radiation may be reflected by the specimen as backscatter and received by at least one radiation detector of the inspection system along the radiation trajectory. Irregularities and various materials of the specimen may produce backscatter radiation at different energies and/or scatter angles which may be identified by employing radiation filters having different attenuation characteristics. By employing these filters in communication with the radiation emitter and the radiation detector, the backscatter radiation passed through the filters may be measured and integrated at different positions of the radiation beam to produce a composite image of the specimen. In this manner, irregularities and associated materials within the specimen may be more easily identified.

In one embodiment, an inspection system is disclosed. The inspection system includes a radiation scanner configured to emit a radiation beam along a radiation trajectory. The inspection system also includes a plurality of filters comprising at least two filters selectably positionable into the radiation trajectory, so that at least one of the at least two filters receives at least a portion of the radiation of the radiation beam and passes attenuated radiation. The at least two filters respectively have different attenuation characteristics. The inspection system also includes a radiation detector configured to receive the attenuated radiation and configured to produce detection data associated with an energy intensity of the attenuated radiation, wherein the received attenuated radiation is backscattered. The inspection system also includes a rendering system configured to create a composite image of a specimen disposed along the radiation trajectory using the detection data from the attenuated radiation passed through the at least two filters. In this manner, irregularities of the specimen may be efficiently identified.

In another embodiment, a method of inspecting a specimen is disclosed. The method includes emitting a radiation beam from a radiation scanner of a backscatter inspection system into a radiation trajectory. The method also includes selectively positioning at least two filters of a plurality of filters of the backscatter inspection system into the radiation trajectory so that at least one of the at least two filters receives at least a portion of the radiation of the radiation beam and passes attenuated radiation. The at least two filters respectively have different attenuation characteristics. The method also includes receiving the attenuated radiation with a radiation detector of the backscatter inspection system and producing detection data associated with an energy intensity of the attenuated radiation. The received attenuated radiation is backscattered from the specimen. The method also includes creating a composite image of the specimen with a rendering system of the backscatter inspection system using the detection data produced from the attenuated radiation passed through the at least two filters. In this manner, the composite image of the specimen may be created with improved contrast to better detect irregularities in the specimen.

In another embodiment, a computer program product is disclosed. The computer program product includes a computer-readable storage medium having computer-readable program code embodied therewith. The computer-readable program code includes computer-readable program code configured to instruct a radiation scanner to emit a radiation beam and along a radiation trajectory. The computer-readable program code also includes computer-readable program code to selectively position at least two filters of a plurality of filters of the backscatter inspection system into the radiation trajectory, so that at least one of the at least two filters receives at least a portion of the radiation of the radiation beam and passes attenuated radiation. The at least two filters respectively have different attenuation characteristics. The computer-readable code also includes computer-readable program code configured to receive detection data produced from a radiation detector of the backscatter inspection system. The radiation detector producing the detection data based on the energy intensity of the attenuated radiation received by the radiation detector, and the received attenuated radiation is backscattered. The computer-readable code also includes computer-readable program code configured to render a composite image of the specimen at a rendering system of the backscatter inspection system using the detection data passed through the at least two filters. In this manner, the specimen may be inspected to distinguish more serious irregularities from more innocuous irregularities of the specimen.

BRIEF DESCRIPTION OF ILLUSTRATIONS

FIG. 1A is a schematic diagram of an exemplary inspection system emitting a radiation beam at a specimen having first and a second components, and a portion of the radiation beam is reflected back from the first and second components as backscatter radiation, the backscatter radiation is attenuated though a first radiation filter of the inspection system, the first radiation filter only permits the backscatter radiation from the first component to be received at a radiation detector of the inspection system, and the radiation detector provides data to be integrated to render a composite image of the specimen;

FIG. 1B is a schematic diagram of the inspection system of FIG. 1B, wherein the backscatter radiation is attenuated though a second radiation filter of the inspection system, the second radiation filter only permits the backscatter radiation from the second component to be received at the radiation detector, and the radiation detector providing data to be integrated to render the composite image of the specimen;

FIGS. 2A through 2D are a perspective view, a front view, left side view, and a top view, respectively, of one embodiment of the inspection system in FIGS. 1A and 1B including a first radiation filter of a plurality of radiation filters receiving the backscatter radiation from the specimen and attenuating a first energy level range of the backscatter radiation in a first arrangement of the plurality of radiation filters;

Figure 1A:
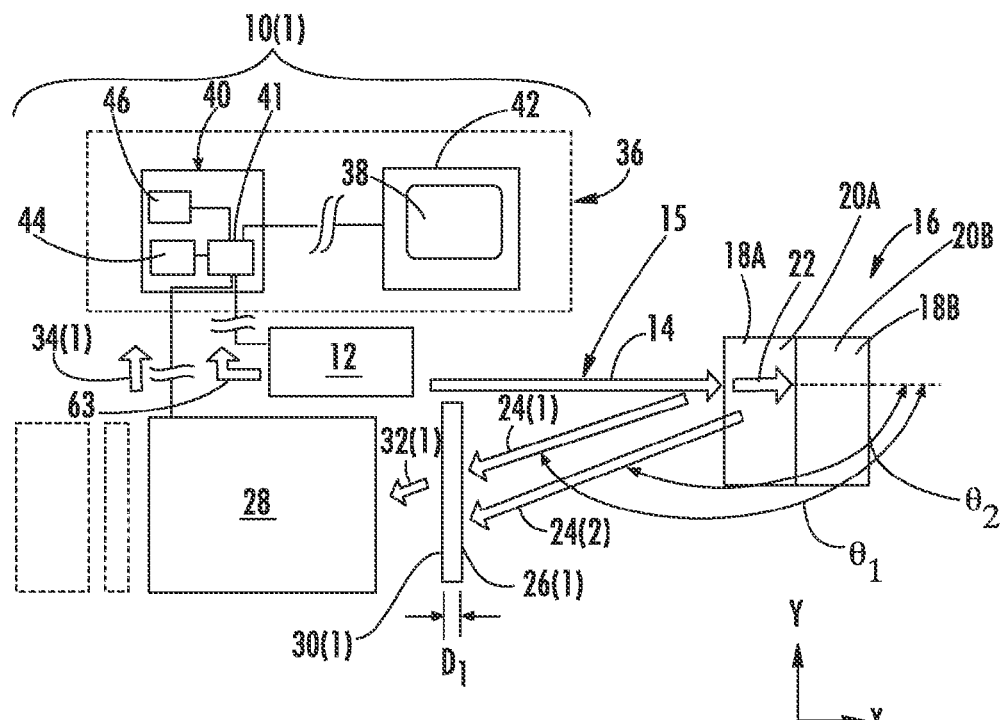
Figure 5A:
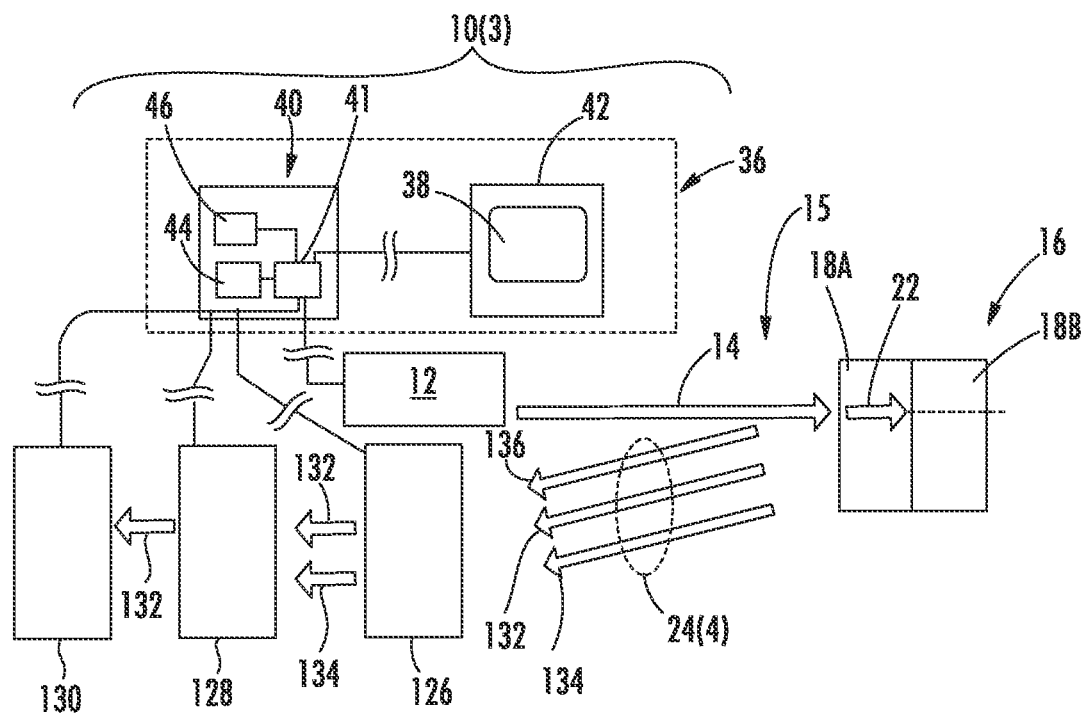
Figure 5B:
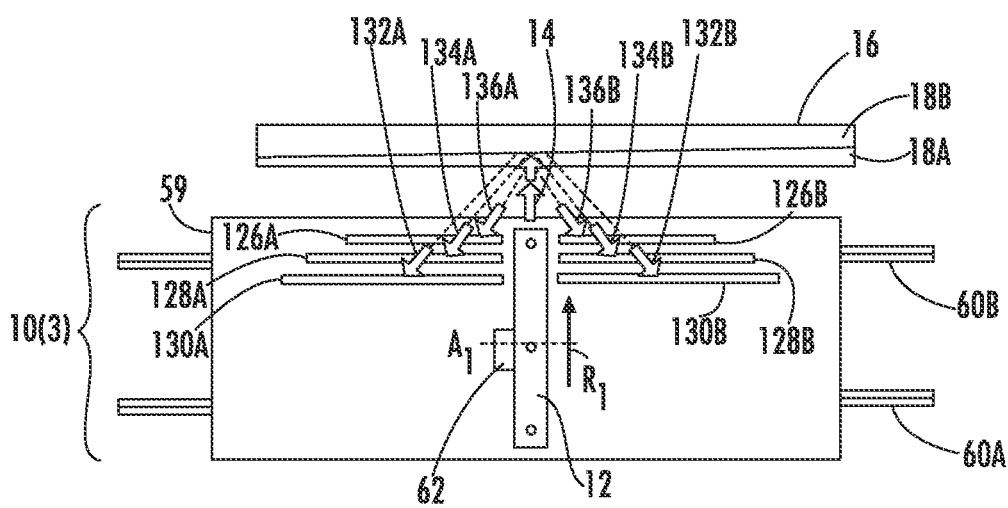
Figure 6A:
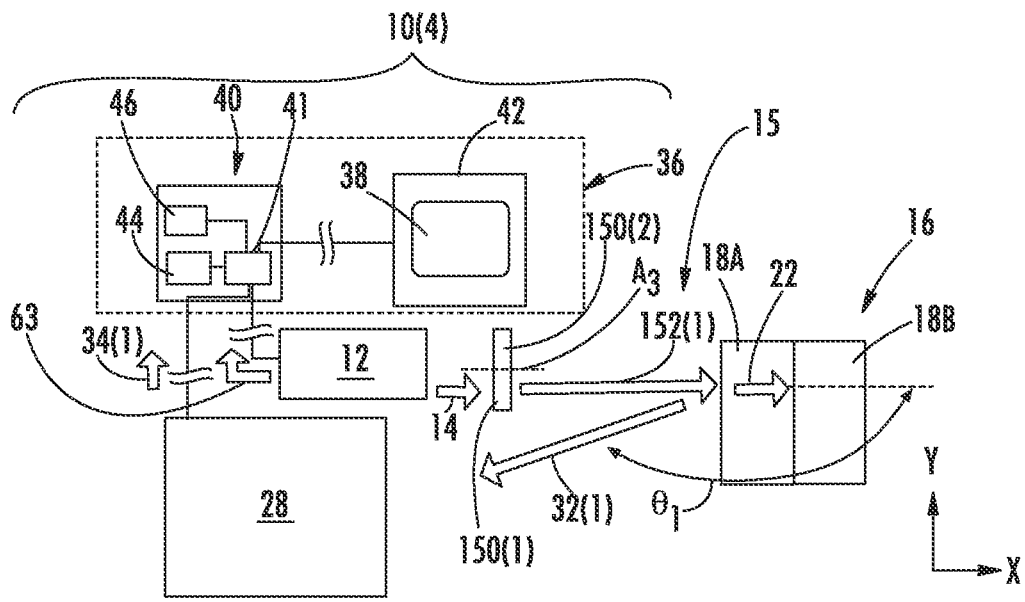
Figure 6B:
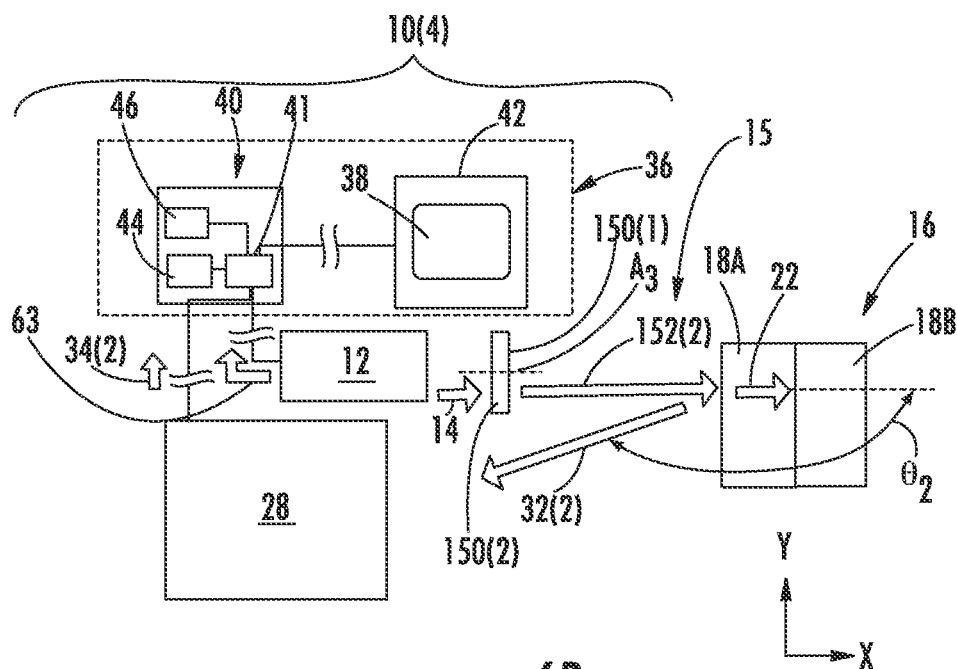

FIGS. 5A and 5B are a schematic view and a top view, respectively, of an inspection system which is a different embodiment of the inspection system of FIG. 1A depicting radiation detectors in a layered arrangement; and FIGS. 6A and 6B are schematic views of another embodiment of an inspection system which includes radiation filters which selectively attenuate the radiation beam prior to the radiation beam being incident upon the specimen.

DETAILED DESCRIPTION

Embodiments enclosed herein include inspection systems employing radiation filters with different attenuation characteristics to determine specimen irregularities, and related methods. An inspection system includes a radiation emitter configured to emit a radiation beam along a radiation trajectory. Some of the radiation may be reflected by the specimen as backscatter and received by at least one radiation detector of the inspection system along the radiation trajectory. Irregularities and various materials of the specimen may produce backscatter radiation at different energies and/or scatter angles which may be identified by employing radiation filters having different attenuation characteristics.

By employing these filters in communication with the radiation emitter and the radiation detector, the backscatter radiation passed through the filters may be measured and integrated at different positions of the radiation beam to produce a composite image of the specimen. In this manner, irregularities and associated materials within the specimen may be more easily identified.

In this regard, FIG. 1A is a schematic diagram of an exemplary inspection system 10(1) including a radiation scanner 12 emitting a radiation beam 14 along a radiation trajectory 15 at a specimen 16. The radiation beam 14 may comprise, for example, x-ray radiation or gamma rays. The radiation beam 14 may be incident upon the specimen 16 which may include a first component 18A and a second component 18B. The first component 18A may comprise a first material 20A, and the second component 18B may comprise a second material 20B having a different atomic number than the first material 20A. For example, the first material 20A may comprise carbon fiber having an atomic number of six (6) and the second material 20B may comprise aluminum having an atomic number of thirteen (13). A portion 22 of the radiation beam 14 may pass through the first component 18A before reaching the second component 18B. In this manner, the first component 18A and the second component 18B may at least partially reflect the backscatter radiations 24(1), 24(2), respectively, at reflection angles theta1 (θ1), theta2 (θ2) towards a radiation filter 26(1) of the inspection system 10(1) along the radiation trajectory 15. It is noted that the radiation trajectory 15 may widen as the backscatter radiations 24(1), 24(2) may have different reflection angles theta1 (θ1), theta2 (θ2).

The compositional and directional differences between the backscatter radiations 24(1), 24(2) may determine whether the backscatter radiations 24(1), 24(2) pass through the backscatter filter 26(1) and reach a radiation detector 28. Specifically, the reflection angles theta1 (θ1), theta2 (θ2) may or may not be the same size and the backscatter radiations 24(1), 24(2) may be reflected from different positions within the specimen 16 along a propagation path of the radiation beam 14. Also, the backscatter radiations 24(1), 24(2) may or may not comprise the same energy level distribution or energy flux. In this regard, the radiation filter 26(1) may comprise a filter material 30(1), for example comprising aluminum, which attenuates at least a portion of the backscatter radiations 24(1), 24(2). The radiation filter 26(1) may have a thickness $D_1$ which may determine how much of the backscatter radiations 24(1), 24(2) may pass through the radiation filter 26(1) to reach the radiation detector 28. The thickness $D_1$ of the radiation filter 26(1) may be, for example, in a range from two-hundred fifty (250) microns to six (6) millimeters. In this manner, a portion 32(1) of the backscatter radiation 24(1) may pass through the radiation filter 26(1) to reach the radiation detector 28 while the backscatter radiation 24(2) may not, as depicted in FIG. 1A. Accordingly, information, in the form of energy intensity and corresponding energy level, contained within the backscatter radiation 24(1) regarding the first component 18A of the specimen 16 may be provided to the radiation detector 28 along the radiation trajectory 15.

Figure 1B:
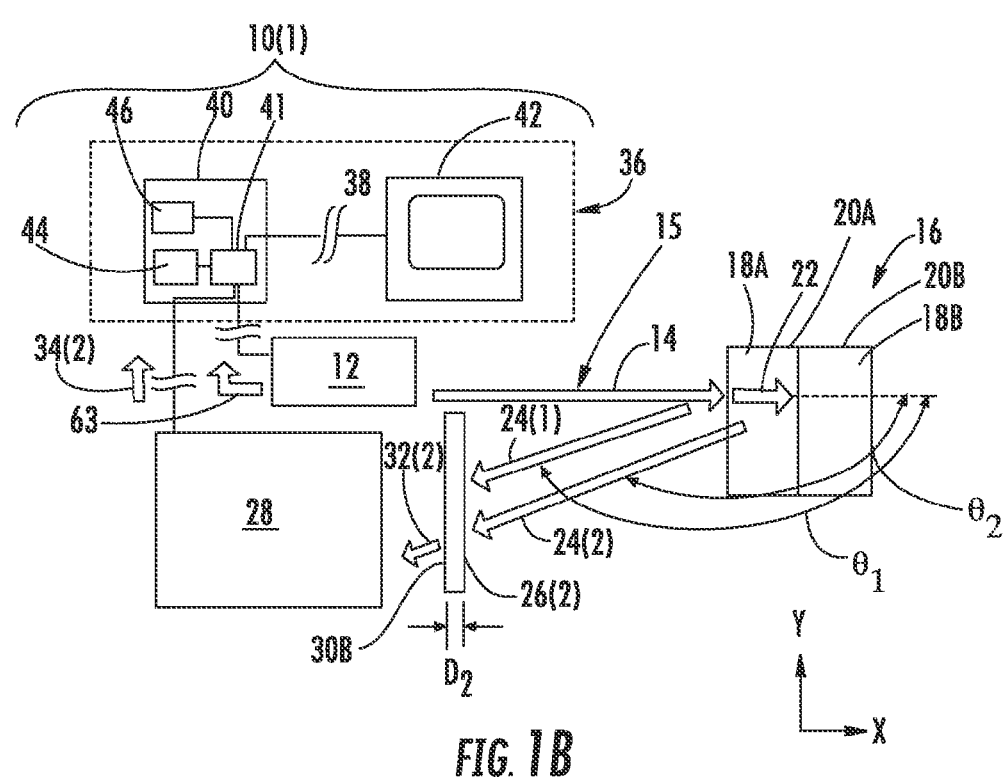

FIG. 1B is a schematic diagram of the inspection system 10(1) of FIG. 1B, wherein the backscatter radiation 24(1), 24(2) from the specimen 16 may be received instead by a second radiation filter 26(2). The backscatter radiation 24(1), 24(2) may be attenuated though the second radiation filter 26(2) of the inspection system 10(1). The radiation filter 26(2) may have a thickness $D_2$ which may determine how much of the backscatter radiation 24(1), 24(2) may pass through the radiation filter 26(2) to reach the radiation detector 28. The thickness $D_2$ of the radiation filter 26(2) may be, for example, in a range from one-hundred fifty (150) microns to four (4) millimeters. In this manner, a portion 32(2) of the backscatter radiation 24(2) may pass through the radiation filter 26(2) to reach the radiation detector 28 while the backscatter radiation 24(2) may not, as depicted in FIG. 1B. Accordingly, information contained within the backscatter radiation 24(2) about the second component 18B of the specimen 16 may be provided to the radiation detector 28 along the radiation trajectory 15.

When the portions 32(1), 32(2) of the backscatter radiation 24(1), 24(2) are received by the radiation detector 28, the radiation detector 28 may measure respective energy flux amounts of the portions 32(1), 32(2). The measured energy flux amounts may be transferred as detection data 34(1), 34(2) to a rendering system 36 of the inspection system 10(1). The rendering system 36 may be adapted to create a composite image 38 of the specimen 16 using the detection data 34(1), 34(2) from the portions 32(1), 32(2) of the attenuated radiation 24(1), 24(2) passed through the radiation filters 26(1), 26(2), respectively. The rendering system 36 may include an electronic assembly 40 comprising a processor 41, memory 44, and a storage device 46. The rendering system 36 may also include a monitor 42 for displaying the composite image 38. Once the composite image 38 is analyzed, characteristics of the specimen 16 are determined, including irregularities and material differences of the specimen 16. In this manner, the composite image 38 for identifying irregularities with the specimen 16 may be created and displayed using the attenuated radiation 24(1), 24(2) passed through the radiation filters 26(1), 26(2).

Another embodiment of an inspection system 10'(1) is provided in FIGS. 2A through 2E. In this regard, FIGS. 2A through 2D are a perspective view, a front view, left side view, and a top view, respectively, of the inspection system 10'(1) which is a different embodiment of the inspection system 10(1). The inspection system 10'(1) includes a first filter 26A(1), 26B(1) of a plurality of radiation filters 26A(1)-26A(N), 26B(1)-26B(N) receiving the backscatter radiation 24 from the specimen 16 and attenuating different energy level ranges of the backscatter radiation 24. In this manner, a composite image 38 of the specimen 16 may be created.

The inspection system 10'(1) may include the radiation scanner 12, the plurality of radiation filters 26A(1)-26A(N), 26B(1)-26B(N), the at least one radiation detector 28A, 28B, and the rendering system 36. Each of these components is discussed sequentially below.

With continued reference to FIGS. 2A through 2E, the radiation scanner 12 may be used to emit a radiation beam 14 to be absorbed, transmitted, and/or reflected by the specimen 16. A portion of the radiation beam 14 reflected from the specimen 16 may be the backscatter radiation 24. The radiation scanner 12 may include a radiation source 48 which may produce, for example, x-ray radiation or gamma ray radiation. The radiation source 48 may be, for example, an x-ray tube manufactured by Yxlon International GmbH of Hamburg, Germany. The radiation source 48 may be disposed within an enclosure 50 having an outer surface 52 providing shielding for the radiation emitted by the radiation source 48. The enclosure 50 may also include inner surfaces 54 connected to the outer surface 52 and forming at least one opening 56 for the radiation produced by the radiation source 48 and emitted from the enclosure 50 as the radiation beam 14. Each of the at least one opening 56 may be of a circular shape and may have a width in a range from 100 microns to two (2) millimeters. In this manner, the radiation beam 14 may be emitted from the radiation scanner 12.

The radiation scanner 12 contributes to the creation of the composite image 38 providing information about irregularities and material of the specimen 16 by moving the radiation beam 14. The composite image 38 may be formed from the backscatter radiation 24 reflected from the specimen 16 as the radiation beam 14 is moved to different positions upon the specimen 16. In this regard, the enclosure 50 may move to direct the radiation beam 14 in a trajectory upon the specimen 16 in a form of a plurality of scans 58 (FIG. 2A) upon the specimen 16 which the radiation beam 14 follows. Each of the scans 58 may be orientated along the z-direction and separated by a separation distance Ds. In one embodiment, the separation distance $D_S$ is in a range from one-hundred fifty (150) to one-thousand (1,000) microns. Movement of the enclosure 50 may be facilitated by a track stage 59 supporting the enclosure 50. The track stage 59 may be movable in a y-direction upon at least one rail 60A, 60B with power provided by, for example, a worm gear (not shown). The track stage 59 may move at a velocity Vy, for example, in an adjustable range from fifty (50) microns per second to one-thousand (1,000) microns per second. The track stage 59 may also include a pivot mechanism 62 (FIG. 2D) to facilitate a rotation $R_1$ of the enclosure 50 about an axis $A_1$. The rotation $R_1$ about the axis $A_1$ enables movement of the at least one opening 56 as well as the radiation beam 14 in the z-direction. The rotation $R_1$ may be, for example, in a range from one-hundred (100) revolutions per second to one (1) revolution per second. The angular position of the rotation $R_1$ of the enclosure 50 and a y-position of the track stage 59 may be forwarded to the rendering system 36 as beam position data 63 to associate a position of the radiation beam 14 to the detection data 34(1), 34(2). In this manner, the radiation beam 14 may move along the scans 58 in the x-direction and the z-direction across the specimen 16 to enable the backscatter radiation 24(1), 24(2) to be produced at different positions of the specimen 16.

Figure 2A:
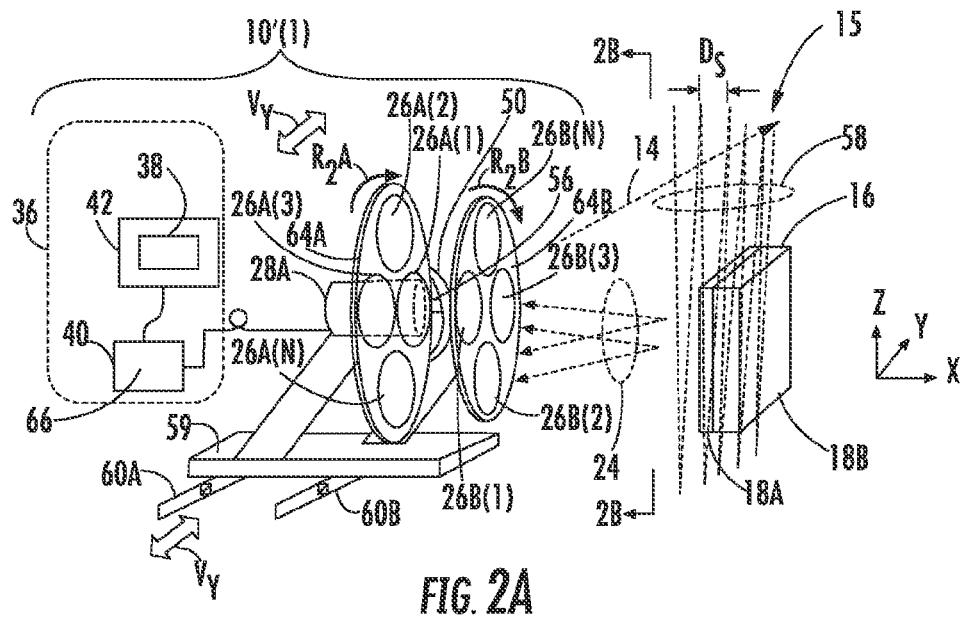
FIG. 2E is a top view of the inspection system in FIG. 2D with a second filter of the plurality of filters receiving the backscatter radiation from the specimen and attenuating a second energy level range of the backscatter radiation in a second arrangement of the plurality of radiation filters.
Figure 2B:
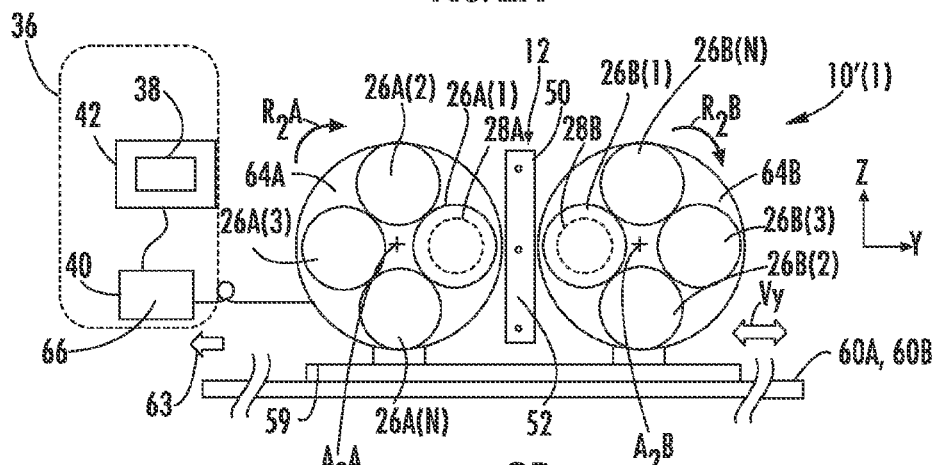
Figure 2C:
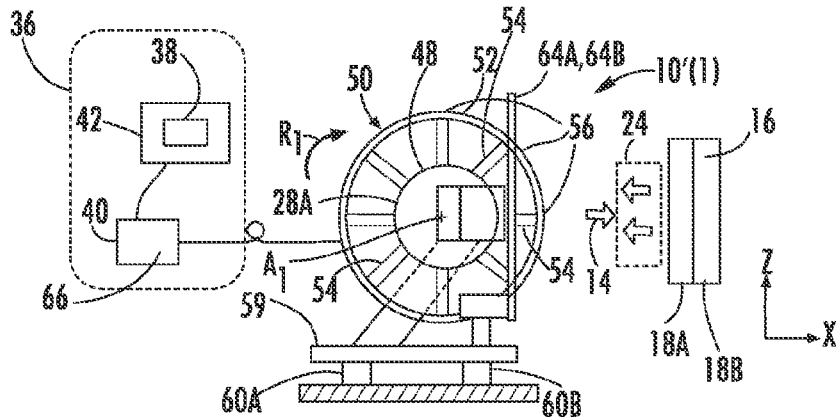
Figure 2D:
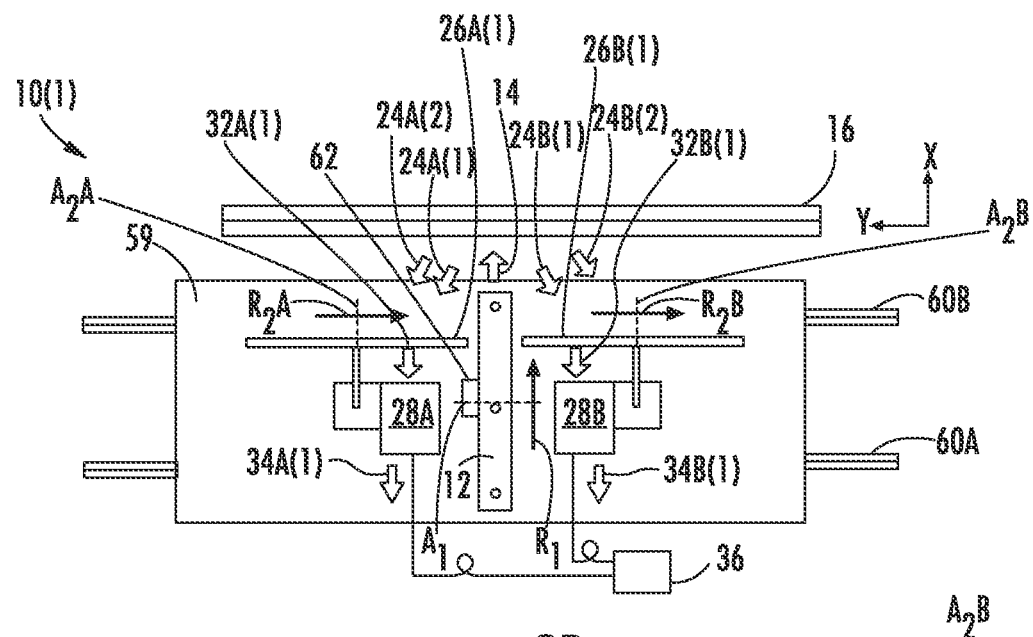
Figure 2E:
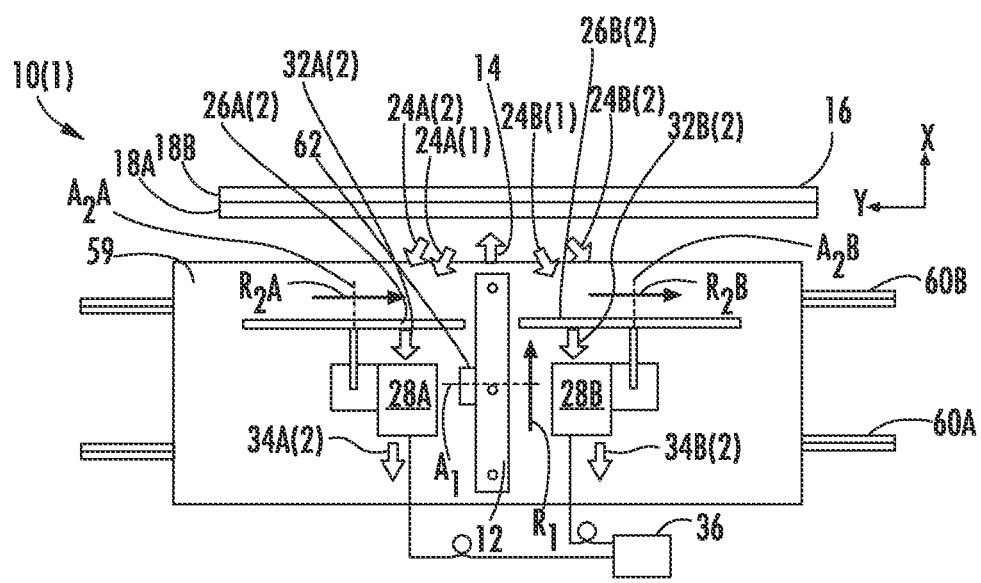

Next, and with continued reference to FIGS. 2A-2E, the radiation filters 26A(1)-26A(N), 26B(1)-26B(N) also contribute to the creation of the composite image 38 by receiving a portion of the radiation beam 14 reflected by the specimen 16 as the backscatter radiation 24 and respectively passing the attenuated radiation 32A(1)-32A(N), 32B(1)-32B(N) to the radiation detectors 28A, 28B. The plurality of filters 26A(1)-26A(N) include at least two filters 26A(1), 26A(2) respectively adapted to attenuate different energy ranges of the backscatter radiation 24(1), 24(2). The at least two filters 26A(1), 26A(2) may be mounted on one or more movable filter mounts 64A, 64B. As shown, the movable filter mounts 64A, 64B are circular-shaped elements disposed side-by-side, one on either side of the radiation scanner 12. The movable filter mounts 64A, 64B may rotate about respective central axes $A_2A$, $A_2B$, respectively, in order to position respective ones of the radiation filters 26A(1)-26A(N), 26B(1)-26B(N) between the at least one radiation detector 28A, 28B and the specimen 16 at different times to produce the attenuated radiation 26A(1)-26A(N), 26B(1)-26B(N). For example, FIGS. 2B and 2D depicts the filters 26A(1), 26B(1) disposed between the radiation detectors 28A, 28B and specimen 16 to pass the attenuated radiation 32A(1), 32B(1). The attenuated radiation 32A(1), 32B(1) received and converted to detection data 34A(1), 34B(1) by the radiation detectors 28A, 28B may be used to create a portion of the composite image 38 associated with that position of the radiation beam 14 upon the specimen 16 as shown in FIG. 2E. The movable filter mounts 64A, 64B may move, for example with a respective rotations $R_2A$, $R_2B$, to dispose the radiation filter 64A, 64B between the respective radiation detectors 28A, 28B and the backscatter radiation 24. The rotations $R_2A$, $R_2B$ may occur continuously or intermittently. For example, the rotations $R_2A$, $R_2B$ may be adapted so that the backscatter radiation 24 from each of the scans 58 may pass through respective ones of the radiation filters 26A(1)-26A(N), 26B(1)-26B(N). In this manner, the attenuated radiation 32A(1)-32A(N), 32B(1)-32B(N) received at each of the radiation detectors 28A, 28B may be more easily associated with respective ones of the radiation filters 26A(1)-26A(N), 26B(1)-26B(N) to simplify the analysis of the radiation by the rendering system 36.

It is noted that the various ones of the radiation filters 26A(1)-26A(N), 26B(1)-26B(N) associated with the attenuated radiation 32A(1)-32A(N), 32B(1)-32B(N) received at each of the radiation detectors 28A, 28B may monitored by the rendering system 36. In some cases different ones of the radiation filters 26A(1)-26A(N), 26B(1)-26B(N) may be used during the same scan 58 to minimize redundant sweeping of the radiation beam 14 over portions of the specimen 16 to increase inspection speed. In another embodiment, only a single one of the radiation filters 26A(1)-26A(N), 26B(1)-26B(N) may be associated with each of the scans 58. In these embodiments, the radiation detectors 28A, 28B may avoid saturation issues that slow the inspection process by changing the energy flux received when different ones of the radiation filters 26A(1)-26A(N), 26B(1)-26B(N) are used.

The radiation detectors 28A, 28B receive the attenuated radiation 32A(1)-32(2), 32B(1)-32B(2) and produce the detection data 34A(1)-34A(2), 34B(1)-34B(2), respectively, which may be sent to the rendering system 36. The radiation detectors 28A, 28B may each be, for example, a sodium iodide (NaI) scintillation detector as manufactured by Horiba Instruments, Inc. of Kyoto, Japan. Other embodiments of the radiation detectors 28A, 28B may comprise at least one plastic scintillation detector. According to particular embodiments, the radiation detector 28A, 28B may have a width in a range from two (2) centimeters to twenty-four (24) centimeters. The radiation detector 28A, 28B may be compatible with attenuated radiation 32(1), 32(2) having an energy level in a range from two (2) keV to two-hundred (200) keV.

In one embodiment, the radiation detectors 28A, 28B and the radiation scanner 12 are disposed on the track stage 59. In this way, the radiation detectors 28A, 28B and the radiation scanner 12 may remain stationary with respect each other as the track stage 59 moves with velocity Vy. In this manner, the radiation detectors 28A, 28B may be positioned to receive the attenuated radiation 32A(1)-32A(N), 32B(1)-32B(N), and then send the detection data 34A(1)-34A(N), 34B(1)-34B(N), respectively, to the rendering system 36.

With continued reference to FIGS. 2A-2E, the rendering system 36 creates the composite image 38 from the detection data 34A, 34B and the beam position data 63. For example, trajectories of the radiation beam 14 may be associated with energy flux at respective distributions of wavelengths of the attenuated radiation 32(1), 32(2) and positions of the radiation filters 26A, 26B included in the detection data 34A, 34B. The rendering system 36 may include the electronic assembly 40 including the processor 41, the memory 44, and the storage device 46. The processor 41 may execute computer software code as part of a software program 66, to associate the detection data 34A(1)-34A(N), 34B(1)-34B(N) with positions of the radiation beam 14. The processor 41 may also serve as a controller configured to operate and coordinate the various configurable and movable components of the inspection system 10'(1), e.g., the track stage 59, the enclosure 50, the plurality of radiation filters 26A(1)-26A(N), 26B(1)-26B(N), and the rendering system 36. In this manner, the composition of the specimen 16 and irregularities associated with the composition may be determined according to the detection data 34A(1)-34A(N), 34B(1)-34B(N) received by the rendering system 36.

Figure 3:
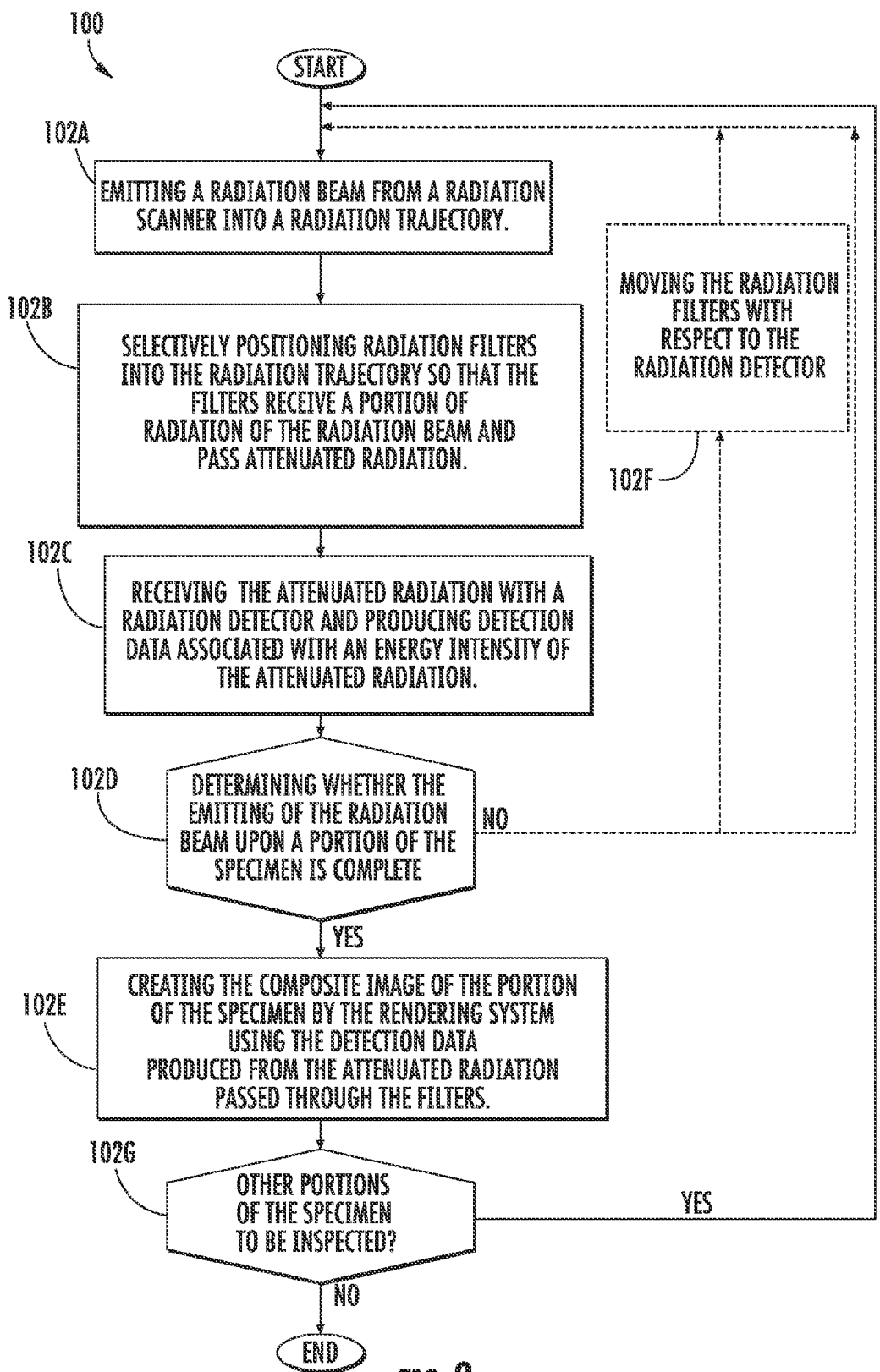
FIG. 3 is a flow chart diagram of an exemplary method for inspecting the specimen with the inspection system of FIG. 1A.

An exemplary method for inspecting the specimen 16 with the inspection system 10'(1) is now discussed. In this regard, FIG. 3 is a flow chart diagram of the method 100 for inspecting the specimen 16 with the inspection system 10'(1) of FIG. 1A. The method 100 may be discussed using the terminology introduced above for consistency and clarity.

The method 100 includes emitting the radiation beam 14 from the radiation scanner 12 into the radiation trajectory 15 (operation 102A of FIG. 3). The method 100 also includes selectively positioning the at least two filters 26A(1), 26A(2) of the plurality of filters 26A(1)-26A(N), 26B(1)-26B(N) into the radiation trajectory 15 so that the at least two filters 26A(1), 26A(2) receive the at least the portion of the radiation of the radiation beam 14 and passes the attenuated radiation 32A(1), 32A(2) (operation 102B of FIG. 3). According to one embodiment, the radiation filters 26A(1), 26A(2) of the radiation filters 26A(1)-26A(N), 26B(1)-26B(N) respectively have different attenuation characteristics. Some of the radiation filters 26A(1)-26A(N), 26B(1)-26B(N) may have attenuation characteristics which minimally attenuates the portion of the radiation beam 14. The method 100 also includes receiving the attenuated radiation 32A(1), 32A(2) with the at least one radiation detector 28 of the inspection system 10'(1) and producing detection data 34A(1), 34A(2) associated with the energy intensity of the attenuated radiation 32A(1), 32A(2) (operation 102C of FIG. 3). The method 100 also includes determining whether the emitting of the radiation beam 14 upon the portion of the specimen 16 is complete (operation 102D of FIG. 3). The method 100 may direct the inspection system 10'(1) to either operation 102E 102F, or 102A based on the determined answer from operation 102D. If operation 102D determines that the emitting may be complete for inspection of the portion of the specimen 16, then the composite image 38 may be created of the portion of the specimen 16 by the rendering system 36 using the detection data 34(1), 34(2) produced from the attenuated radiation passed through the at least two filters 26A(1), 26A(2) (operation 102E of FIG. 3). Otherwise, the inspection system 10'(1) may emit the radiation beam 14 upon a radiation trajectory 15 over the portion of the specimen 16 (operation 102A) or may also move the filters 26A, 26B with respect to the radiation detector 28 to enable selectable ones of the plurality of filters 26A(1)-26A(N), 26B(1)-26B(N) to pass attenuated radiation to the radiation detector 28 (operation 102F of FIG. 3). In this manner, a wide variety of information included as part of the backscattered radiation 24 of the specimen 16 may be associated with different ones of the radiation filters 26A(1)-26A(N), 26B(1)-26B(N) and irregularities may be more easily identified by comparing the received values of the attenuated radiation 32A(1)-32A(N), 32B(1)-32B(N) as the radiation beam 14 sweeps over the specimen 16.

It is noted that the method 100 may also include determining whether other portions of the specimen 16 are to be inspected (operation 102G of FIG. 3). If additional portions of the specimen 16 are to be inspected, then the inspection system 10'(1) may emit and sweep the radiation beam 14 across the other portions of the specimen 16 (operation 102A of FIG. 3). Otherwise, the method 100 may end. In this manner, the portions of the specimen 16 to be inspected may be evaluated by the inspection system 10'(1) to determine irregularities and related material compositions of the specimen 16.

Figure 4A:
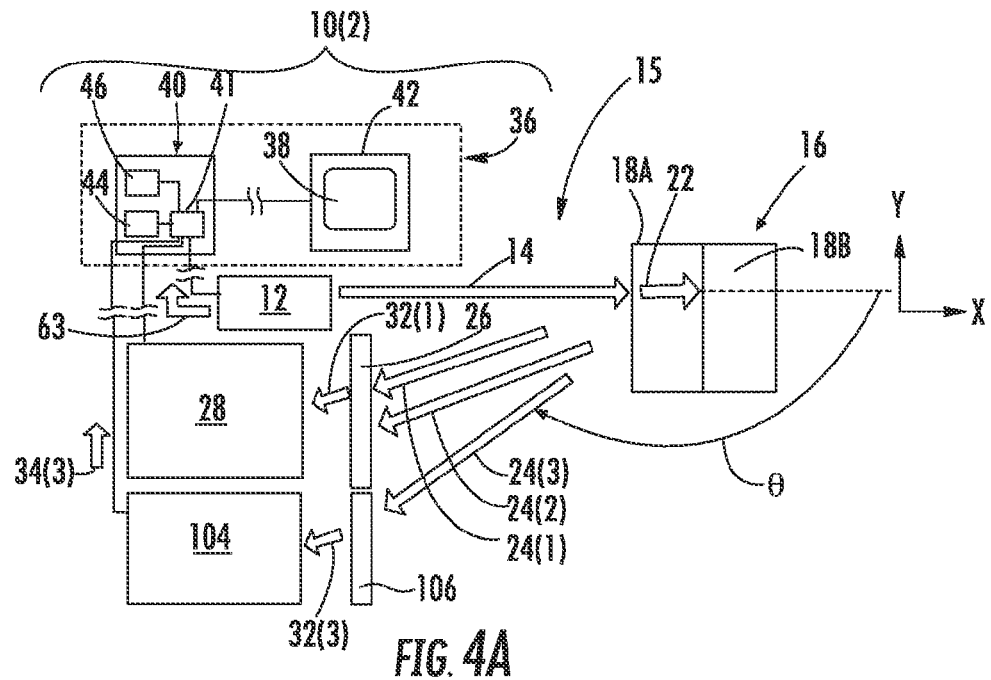
FIGS. 4A and 4B are a schematic view and a top view, respectively, of an inspection system which is a different embodiment of the inspection system of FIG. 1A and includes filters at different angular positions relative to a radiation beam emitted from the inspection system to discriminate between backscatter radiation with different reflection angles.

Referring now to FIG. 4A, a schematic view of another embodiment of an inspection system 10(2) is shown. The embodiment of FIG. 4A is similar to the inspection systems 10(1), 10'(1), so only the differences will be discussed for clarity and conciseness. The inspection system 10(2) includes at least one filter 106 at a different angular position (theta) relative to the radiation beam 14 emitted from the inspection system 10(2) compared to the filters 26A, 26B. The inspection system 10(2) also includes a radiation detector 104 which is disposed to receive attenuated radiation 32(3) which is passed through the filter 106. The radiation detector 104 may provide detection data 34(3) to the rendering system 36, where the information provided by the attenuated radiation 32(3) may be analyzed to better determine irregularities of the specimen 16.

Figure 4B:
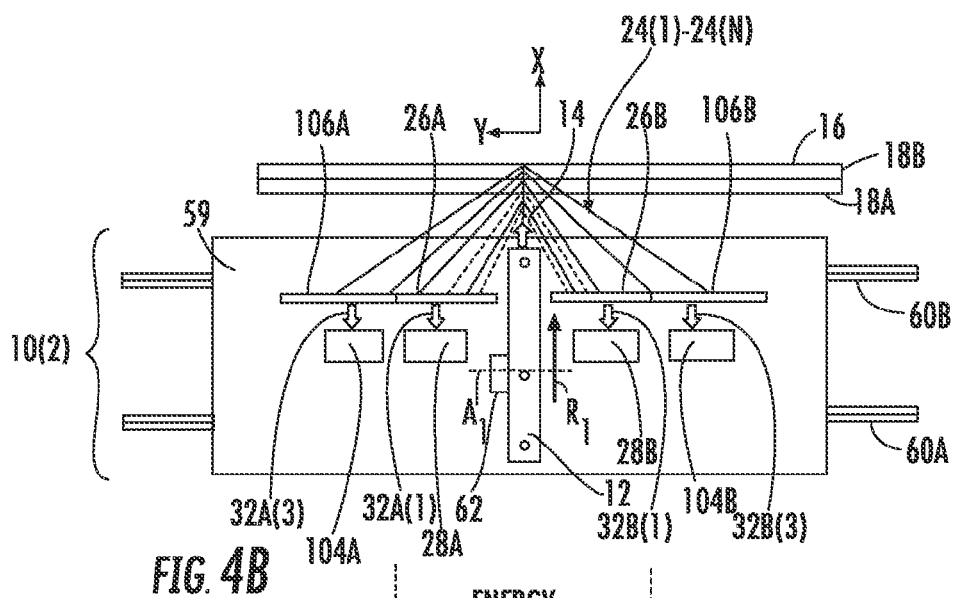

FIG. 4B is a top view of the inspection system 10(2) of FIG. 4A depicting backscatter radiation 24(1)-24(N) reflected from the specimen 16. The rendering system 36 is hidden from view to emphasize other features of the inspection system 10(2). In this regard, the backscatter radiation 24(1)-24(N) is received by the filters 26A, 26B, 106A, 106B at the different angular positions (theta) relative to the radiation beam 14. The filters 106A, 106B pass attenuated radiation 32A(3), 32B(3), respectively, to the radiation detectors 104A, 104B. In this manner, backscatter radiation 24A(3), 24B(3) directed at a reflection angle (theta) more flared from the radiation beam 14 may be received by the inspection system 10(2).

Figure 4C:
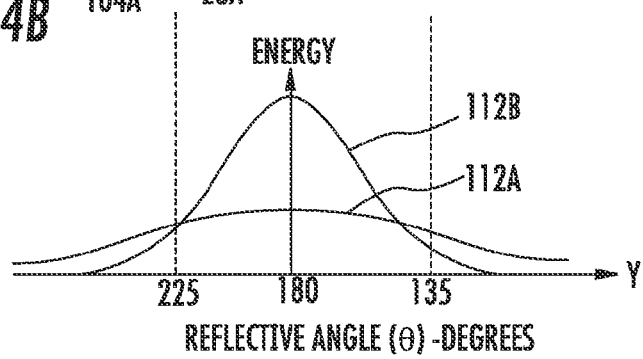
FIG. 4C is a graph depicting two (2) distributions of energy backscattered from the specimen of FIG. 4B, wherein the two (2) distributions include respectively a 2.75 keV portion and a 511 keV portion of the backscattered radiation.

The reflection angle (theta) of the backscatter radiation 24(1)-24(N) may provide information regarding the presence of different characteristics of the specimen 16. In this regard, FIG. 4C is a graph depicting two (2) distributions of energy backscattered from the specimen 16 of FIG. 4B, wherein the two (2) distributions include respectively a higher energy portion 112A including a 511 keV energy portion of the backscattered radiation 24(1)-24(N) and a lower energy portion 112B including a 2.75 keV energy portion of the backscattered radiation 24(1)-24(N). The lower energy portion 112B may preferentially backscatter with a reflection angle (theta) near 180 degrees, as opposed to the side, for example, near 90 degrees. In contrast, the higher energy portion 112A scatter more uniformly over a wide range of reflection angles (theta). In this manner, the radiation detectors 104A, 104B may be disposed in a manner to preferentially receive energy portions of the backscatter radiation 24(1)-24(N) that reflect from the specimen 16 at various predetermined reflection angles (theta) to isolate energy portions of the backscatter radiation which contain specific information to the irregularities and associated material compositions of the specimen 16.

In this regard, a practical use for having the radiation detectors at different angles (theta) may be to selectively filter different types of irregularities of the specimen 16. When the specimen 16 includes multiple material types, each of the material types may reflect different energies and at different reflection angles (theta) relative to the radiation beam 14. For example, the specimen 16 may include the inner portion 18B including a metal material which may be covered with the outer portion 18A of composite materials. The outer portion 18A including the composite materials may reflect the lower energy portion 112B narrowly near the radiation beam 14 and this lower energy portion 112B may be selectively received by the radiation detectors 28A, 28B in a range of reflection angles (theta) from 135 degrees to 225 degrees. Any irregularities related to the portion 18A of the specimen 16 may be discerned from the backscatter radiation received from the portion 18B of the specimen 16. In this regard, one or more of the radiation filters 26A, 26B may be configured to attenuate the higher energy portion 112A to focus on information provided by the lower energy portion 112B.

The inspection system 10(2) includes other features to discern irregularities and material compositions of the inner portion 18B of the specimen 16. The higher energy portion 112A of the radiation beam 14 may mostly pass through the outer portion 18A of the specimen 16 to be incident upon the inner portion 18B of the specimen 16 as represented by the portion 22 of the radiation beam 14 in FIG. 4A. Unlike the outer portion 18A, the inner portion 18B of the specimen 16, including the metal material, may be more reflective to the higher energy portion 112A of the radiation beam 14 and the higher energy portion 112A may be reflected from the inner portion 18B with a relatively uniform distribution along reflection angles as depicted in FIG. 4C. Specifically, the higher energy portion 112A may also preferentially reflect with a wide range of reflection angles (theta), including values less than 135 degrees and more than 225 degrees where the higher energy portion 112A is more predominantly reflected in comparison to the lower energy portion 112B. The radiation filters 106A, 106B may be configured to attenuate the lower energy portion 112B to focus on information provided by the higher energy portion 112A. In this manner, as the radiation beam 14 may be emitted and swept across portions of the specimen, changes in the lower energy portion 112B received at the radiation detectors 28A, 28B may indicate irregularities in the outer portion 18A of the specimen whereas changes in the higher energy portion 112A received at the radiation detectors 104A, 104B may indicate irregularities in the inner portion 18B of the specimen 16.

FIGS. 5A and 5B are a schematic view and a top view, respectively, of an inspection system 10(3). The inspection system 10(3) is similar to the inspection system 10(1) and so only the differences will be discussed for clarity and conciseness. The inspection system 10(3) may include radiation detectors 126, 128, 130 in a layered arrangement relative to the direction of the backscattered radiation 24(4). The radiation detectors 126, 128, 130 may serve as layered filters which are selective, so that the backscattered radiation 24(4) may pass through various ones of the radiation detectors 126, 128, 130 depending upon respective energy distribution of the backscatter radiation 24(4). For example, a higher energy portion 132 of the backscatter radiation 24(4) may pass through the radiation detectors 126, 128 to be captured and measured at the radiation detector 130. A medial energy portion 134 of the backscatter radiation 24(4) may pass through the radiation detector 126 to be captured and measured at the radiation detector 128 and a lower energy portion 136 of the backscatter radiation 24(4) may be captured and measured at the radiation detector 126. In this manner, the inspection system 10(3) may facilitate selective filtering of the backscatter radiation 24(4) to discriminate between various materials of the specimen 16 and/or irregularities which may scatter back at different energies.

It is noted that in FIG. 5B the inspection system 10(3) may include the track stage 59, with the radiation detectors 126, 128, 130 disposed thereon. In this way, the track stage 59 can move the radiation detectors along the y-axis. In one embodiment, the radiation detector 126 may be made up of a plurality of radiation detectors. For example, as illustrated in FIG. 5B, the radiation detector 126 includes two radiation detectors 126A, 126B located on opposite sides of the radiation scanner 12. Likewise, the radiation detector 128 may include radiation detectors 128A, 128B and the radiation detector 130 may include radiation detectors 130A, 130B, where each of the constituent radiation detectors are located on opposite sides of the radiation scanner 12. In this manner, the inspection system 10(3) may identify irregularities of the specimen 16 using the backscatter radiation 24(4) reflected on opposite sides of the radiation beam 14 of the radiation scanner 12.

FIGS. 6A and 6B are schematic views of an inspection system 10(4). The inspection system 10(4) is similar to the inspection system 10(1) and so only the differences will be discussed for clarity and conciseness. Instead of including the radiation filters 26A(1)-26A(N), 26B(1)-26B(N) attenuating the backscatter radiation 24, the inspection system 10(4) includes radiation filters 150(1), 150(2) which selectively attenuate the radiation beam 14 prior to being incident upon the specimen 16. In this regard, FIG. 6A depicts the radiation filter 150(1) being used to attenuate the radiation beam 14 to pass attenuated radiation 152(1) which may be reflected from the specimen 16 as backscattered attenuated radiation 32(1) (compare to FIG. 1A). FIG. 6B depicts the radiation filter 150(2) displacing the radiation filter 150(1) by, for example, translation or rotation about an axis of rotation $A_3$ so that the radiation filter 150(2) is positioned to attenuate the radiation beam 14, resulting in attenuated radiation 152(2) being propagated to specimen 16. Attenuated radiation 152(2) is then reflected as backscatter from the specimen 16 as the attenuated radiation 32(2) (compare to FIG. 1B). The this manner, the attenuated radiation 32(1), 32(2) may be alternatively received by the radiation detector 28 to be analyzed by the rendering system 36 to determine irregularities and associated material compositions of the specimen 16.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. In one example, the specimen 16 may be an aircraft wing having the outer portion 18A be an aircraft skin made of composite and the inner portion 18B being an aircraft structural member (or "spar") made of aluminum or other metal. In some embodiments, it is recognized that the inspection system could include optical equipment like beam steering components (e.g., reflective mirrors or refractive lenses), focusing lenses, collimators, filters, and/or others to steer the radiation along a radiation trajectory. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform aspects of the present invention.

These computer-readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. An inspection system, comprising:
   a radiation scanner configured to emit a radiation beam along a radiation trajectory;
   a plurality of filters comprising at least two filters selectably positionable so that at least one of the at least two filters receives at least a portion of the radiation of the radiation beam backscattered from a specimen and passes attenuated radiation, wherein the at least two filters respectively have different attenuation characteristics;
   a radiation detector configured to receive the attenuated radiation and configured to produce detection data associated with an energy intensity of the attenuated radiation; and
   a rendering system configured to create a composite image of the specimen disposed along the radiation trajectory using the detection data from the attenuated radiation passed through the at least two filters.

2. The system of claim 1, wherein the plurality of filters are movable with respect to the radiation detector to enable selectable ones of the at least two filters to pass attenuated radiation to the radiation detector.

3. The system of claim 2, wherein in a first arrangement of at least two arrangements the radiation detector is configured to exclusively receive the attenuated radiation from a first filter of the at least two filters.

4. The system of claim 3, wherein in a second arrangement of the at least two arrangements the radiation detector is configured to exclusively receive the attenuated radiation from a second filter of the at least two filters.

5. The system of claim 1, wherein a first filter of the at least two filters comprises aluminum of a thickness less than one millimeter, and a second filter of the at least two filters comprises aluminum of a thickness greater than the thickness of the first filter.

6. The system of claim 2, wherein the at least two filters are selectively positionable in a portion of the radiation trajectory to receive the at least the portion of the radiation backscattered from the specimen.

7. The system of claim 1, wherein the plurality of filters include layered filters which are arranged so that a first radiation detector of the radiation detector receives attenuated radiation solely from a first layered filter of the layered filters, and a second radiation detector of the radiation detector receives attenuated radiation passed through the first layered filter and a second layered filter of the layered filters.

8. The system of claim 1, further comprising a track stage to move the radiation scanner relative to the specimen.

9. The system of claim 1, wherein the plurality of filters are included as part of at least one movable filter mount.

10. A method of inspecting a specimen, comprising:
    emitting a radiation beam from a radiation scanner of a backscatter inspection system into a radiation trajectory;
    selectively positioning at least two filters of a plurality of filters of the backscatter inspection system so that at least one of the at least two filters receives at least a portion of the radiation of the radiation beam backscattered from the specimen and passes attenuated radiation, wherein the at least two filters respectively have different attenuation characteristics;
    receiving the attenuated radiation with a radiation detector of the backscatter inspection system and producing detection data associated with an energy intensity of the attenuated radiation; and
    creating a composite image of the specimen with a rendering system of the backscatter inspection system using the detection data produced from the attenuated radiation passed through the at least two filters.

11. The method of claim 10, wherein the selectively positioning comprises moving the at least two filters with respect to the radiation detector to enable selectable ones of the at least two filters to pass attenuated radiation to the radiation detector while the at least two filters are respectively disposed in at least two arrangements.

12. The method of claim 11, wherein the receiving the attenuated radiation comprises the radiation detector exclusively receiving the attenuated radiation from a first filter of the at least two filters in a first arrangement of the at least two arrangements.

13. The method of claim 12, wherein the receiving the attenuated radiation comprises the radiation detector exclusively receiving the attenuated radiation from a second filter of the at least two filters in a second arrangement of the at least two arrangements.

14. A non-transitory computer-readable storage medium containing computer-readable program code that, when executed by operation of one or more computer processors, performs an operation comprising:

instructing a radiation scanner of a backscatter inspection system to emit a radiation beam and along a radiation trajectory;

selectively positioning at least two filters of a plurality of filters of the backscatter inspection system so that at least one of the at least two filters receives at least a portion of the radiation of the radiation beam backscattered from a specimen and passes attenuated radiation, wherein the at least two filters respectively have different attenuation characteristics;

receiving detection data produced from a radiation detector of the backscatter inspection system, the radiation detector producing the detection data based on an energy intensity of the attenuated radiation received by the radiation detector; and rendering a composite image of the specimen at a rendering system of the backscatter inspection system using the detection data passed through the at least two filters.

15. The computer-readable storage medium of claim 14, wherein the computer-readable program code, when executed by operation of the one or more computer processors, performs further operations comprising:

instructing a movement of the at least two filters with respect to the radiation detector to enable selectable ones of the at least two filters to pass attenuated radiation to the radiation detector while the at least two filters are respectively disposed in at least two arrangements.

16. The computer-readable storage medium of claim 15, wherein the computer-readable program code, when executed by operation of the one or more computer processors, performs further operations comprising:

instructing a movement of the at least two filters to a first arrangement of the at least two arrangements wherein in the first arrangement the radiation detector exclusively receives the attenuated radiation from a first filter of the at least two filters.

17. The computer-readable storage medium of claim 16, wherein the computer-readable program code, when executed by operation of the one or more computer processors, performs further operations comprising:

instructing a movement of the at least two filters to a second arrangement of the at least two arrangements wherein in the second arrangement the radiation detector exclusively receives the attenuated radiation from a second filter of the at least two filters.

18. The computer-readable storage medium of claim 14, wherein the computer-readable program code, when executed by operation of the one or more computer processors, performs further operations comprising:

instructing a movement of the radiation scanner in a direction angled to the radiation beam.

* * * * *